United States Patent
Nyman et al.

(10) Patent No.: US 12,053,592 B2
(45) Date of Patent: *Aug. 6, 2024

(54) URINARY CATHETER HAVING A SOFT TIP

(71) Applicant: DENTSPLY IH AB, Mölndal (SE)

(72) Inventors: Martin Nyman, Kallered (SE); Niklas Dahlberg, Gothenburg (SE)

(73) Assignee: DENTSPLY IH AB, Molndal (SE)

(*) Notice: Subject to any disclaimer, the term of this patent is extended or adjusted under 35 U.S.C. 154(b) by 565 days.

This patent is subject to a terminal disclaimer.

(21) Appl. No.: 17/149,545

(22) Filed: Jan. 14, 2021

(65) Prior Publication Data

US 2021/0162172 A1 Jun. 3, 2021

Related U.S. Application Data

(63) Continuation of application No. 14/975,964, filed on Dec. 21, 2015, now Pat. No. 10,905,852.

(30) Foreign Application Priority Data

Dec. 29, 2014 (EP) .................................... 14200366

(51) Int. Cl.
*A61M 25/00* (2006.01)

(52) U.S. Cl.
CPC ...... *A61M 25/0068* (2013.01); *A61M 25/001* (2013.01); *A61M 25/0017* (2013.01); *A61M 2025/0081* (2013.01)

(58) Field of Classification Search
CPC ............ A61M 25/0068; A61M 25/001; A61M 25/0017; A61M 2025/0081
See application file for complete search history.

(56) References Cited

U.S. PATENT DOCUMENTS

| 3,983,879 | A | 10/1976 | Todd |
| 4,773,901 | A | 9/1988 | Norton |
| 5,584,821 | A | 12/1996 | Hobbs et al. |
| 5,628,770 | A | 5/1997 | Thome et al. |
| 6,004,305 | A | 12/1999 | Hursman et al. |

(Continued)

FOREIGN PATENT DOCUMENTS

| AU | 503664 B2 | 9/1979 |
| CN | 1171057 A | 1/1998 |

(Continued)

OTHER PUBLICATIONS

Office Action mailed Jul. 7, 2022 for Korean Patent Application No. 10-2017-7020736.

(Continued)

*Primary Examiner* — Ariana Zimbouski
(74) *Attorney, Agent, or Firm* — Perkins Coie LLP

(57) ABSTRACT

A urinary catheter is disclosed, comprising a tubular shaft extending between an insertable end and a discharge end, and a tip fixedly connected to said insertable end of the tubular shaft. The tip has an outer diameter which at all places is equal to or lower than the outer diameter of the tubular shaft, and is very soft, so that the hardness of the tip is equal to or lower than 60 micro Shore A. It has been found that such a soft tip provides a catheter which is easier to insert into the urethra, in particular in urethras providing various types of obstacles. A corresponding method of manufacturing is also disclosed.

24 Claims, 3 Drawing Sheets

(56) References Cited

U.S. PATENT DOCUMENTS

| | | |
|---|---|---|
| 8,168,249 B2 | 5/2012 | Utas et al. |
| 2002/0173741 A1 | 11/2002 | Rioux |
| 2004/0181235 A1 | 9/2004 | Daignault et al. |
| 2004/0193143 A1 | 9/2004 | Sauer |
| 2005/0049575 A1 | 3/2005 | Snel |
| 2008/0281291 A1* | 11/2008 | Tihon ............... A61M 25/0017 604/517 |
| 2010/0063477 A1* | 3/2010 | Ohigawa ............ B29C 66/8122 156/60 |
| 2012/0158025 A1 | 6/2012 | Anderson et al. |
| 2012/0191073 A1 | 7/2012 | Utas et al. |
| 2014/0018833 A1 | 1/2014 | Zhou |
| 2015/0297862 A1 | 10/2015 | Sadik |

FOREIGN PATENT DOCUMENTS

| | | |
|---|---|---|
| CN | 101222946 A | 7/2008 |
| CN | 101998867 A | 3/2011 |
| CN | 102488955 A | 6/2012 |
| EP | 0093093 A1 | 11/1983 |
| EP | 0217771 A1 | 4/1987 |
| EP | 0384476 A1 | 8/1990 |
| EP | 0799069 A1 | 10/1997 |
| EP | 1149598 A2 | 10/2001 |
| GB | 1467976 A | 3/1977 |
| JP | 05305143 | 11/1993 |
| WO | 9749437 A1 | 12/1997 |
| WO | 2005094665 A2 | 10/2005 |
| WO | 2006069396 A1 | 6/2006 |
| WO | 2009059220 A1 | 5/2009 |
| WO | 2011036162 A2 | 3/2011 |
| WO | 2014022227 A1 | 2/2014 |

OTHER PUBLICATIONS

Office Action for Chinese Patent Application No. 201580069799.2, mailed Nov. 20, 2019 (20 pages).

Korean Patent Office, Office Action dated Jan. 31, 2023 for Korean Patent Application No. 10-2017-7020736, 14 pages with English translation.

* cited by examiner

URINARY CATHETER HAVING A SOFT TIP

CROSS REFERENCE TO RELATED APPLICATIONS

This patent document is a continuation of and claims the benefit of priority to U.S. patent application Ser. No. 14/975,964, filed on Dec. 21, 2015, which claims the benefit of priority to European Patent Application No. 14200366.4, filed on Dec. 29, 2014. The entire contents of the before-mentioned patent applications are incorporated by reference as part of the disclosure of this application.

FIELD OF THE INVENTION

The present invention generally relates to a urinary catheter comprising a tubular shaft extending between an insertable end and a discharge end, and having a tapering tip fixedly connected to the insertable end of the tubular shaft. The invention is also related to a corresponding method of manufacture and use.

BACKGROUND OF THE INVENTION

The present invention relates to a urinary catheter assembly, and in particular for urinary hydrophilic catheters. Urinary catheters are commonly used for draining urine from the bladder. One type of urinary catheters is indwelling catheters, so-called Foley catheters, which are maintained in place in the urethra for an extended period of time, such as for days, weeks or even months. Another type of urinary catheters are intended for short term use, so-called intermittent catheters. Intermittent urinary catheters are used for draining the bladder once, and then be removed. Intermittent catheters are typically used for a few minutes, and catheterization is typically made by the user him/her self so-called self-catheterization, and is typically performed many times a day. In order to maintain the catheter in a clean and preferably sterile condition, each catheter is normally pre-packed in a receptacle by the manufacturer, thereby providing a catheter assembly. Typically catheters for intermittent catheterization are used by patients suffering from urinary incontinence or by disabled individuals like para- or tetraplegics. Using an intermittent catheter, the bladder may be drained through a natural or artificial urinary canal. Many catheters for intermittent catheterization are provided with a hydrophilic coating or the like, providing a smooth and slippery surface when wetted, for safe and comfortable insertion in the urinary canal.

Many hydrophilic catheter assemblies include a supply of wetting fluid, either in direct contact with the catheter or in a separate compartment, for clean and convenient activation of the hydrophilic surface before use.

Because of the intended use of such medical devices certain parameters need to be satisfied by the material from which the elongate shaft is manufactured. The material must fulfill such requirements as softness, good kink resistance, good dimensional stability, processability, for example ease to form and glue, and the possibility to be sterilized by radiation, steam, ethylene oxide or other means. For some products, there is further the need for the material to accept a surface treatment which will impart desired surface properties to the medical device, such as hydrophilicity. To this latter end, the chemistry of the substrate material is critical since this affects the possibility to coat the substrate.

For many years now polyvinyl chloride (PVC) has been used to manufacture urinary catheters, and in particular the elongate shaft. For instance, EP 0 093 093 by the same applicant makes known a process for manufacturing a PVC urinary catheter having a hydrophilic outer surface coating which exhibits a low coefficient of friction when wetted.

However, the suitability of PVC for medical devices such as catheters is now being questioned on environmental grounds and further because of the toxicity of the plasticizers added to PVC. Moreover, coating PVC catheters by, for example, the EP 0 093 093 results in an appreciable shrinkage of the PVC catheters in the longitudinal direction, typically 6-7% of the original length, due to the operating temperatures used in the coating process.

Other substrate materials have also been proposed and used. For example, WO 97/49437 by the same applicant proposes to use a polyether block amide or a styrene block copolymer as substrate material for a hydrophilic catheter. These materials have proven to be suitable for hydrophilic coating, and to have adequate mechanical and chemical properties. However, a problem with these materials is that these materials are relatively expensive to manufacture. Further, polyether block amide has relatively high resilience, which makes it unsuitable for certain applications. For example, catheters made of this material may be difficult to handle for disabled patients. When using styrene block copolymer, the adherence of surface coatings, such as hydrophilic coatings, is lower than when using e.g. polyether block amide.

Further, US 2012/0191073 and U.S. Pat. No. 8,168,249, also by the same applicant, describes the use of a polymer blend to form the substrate of the catheter shaft, the blend being primarily based on polyolefin, but with an addition of a polymer having active hydrogen(s), such as polyamide or polyurethane.

However, insertion of a urinary catheter into the urethra is often cumbersome, and associated with certain risks. This is particularly the case for male catheters. A male catheter is relatively long, typically 35-40 cm, to be able to extend through the whole length of the urethra. The insertable length of the catheter is normally at least 200-350 mm for male users. The male urethra is also curved in many places, and comprises sections with reduced cross-sections. Thus, during the introduction of the catheter into the urethra and while guiding the catheter tip through the urethra into the bladder, it is necessary to overcome pockets, folds, bends, strictures, and/or the like. If one pushes the catheter with a corresponding force against the existing impediments in the urethra, one will face a considerable risk of injury.

To overcome such insertion problems, it is known to use special tips on the catheter. For example, the catheter may be provided with a curved tip, often referred to as a Tiemann or Coudé type catheter. Tiemann and Coudé catheters have a tip which is angled upward, to assist in negotiating the male prostatic curve. Thus, this tip form facilitates passage through the bladder neck in the presence of obstruction e.g. from a slightly enlarged prostate gland (e.g. in benign prostatic hyperplasia), and can be helpful for such and other difficult insertions. Such tips are e.g. known from EP 0 799 069 by the same applicant.

Further, EP 0 384 476, provides catheters with a special catheter tip. This catheter tip is made somewhat flexible or elastic, and conically tapers toward its free end, and is rounded at its front or free end. Although this specific configuration permits pushing the catheter through the urethra into the bladder, while overcoming the aforesaid problem locations, it also presents in this instance a significant risk of injury because of the necessary application of force.

Still further, US 2004/193143 discloses a catheter having an enlarged, ball-shaped tip, having a diameter widely exceeding the diameter of the rest of the catheter shaft. This catheter tip expands the urethra because of its configuration with the rounded, spherical head portion, so that pockets, folds, and bends are supposedly simpler to overcome. However, it has been found that this type of catheter, which is also commercially available under the trade name IQ-Cath, has certain problems, such as finding its way around the prostate.

However, despite these attempts, insertion of a catheter into the urethra of many male users is often still problematic and dangerous. There is therefore a need for a catheter which is easier to handle, and which reduces the risk of injury, when being pushed into and through the urethra.

SUMMARY OF THE INVENTION

It is a general object of the present invention to alleviate the above-discussed problems.

This problem is solved by means of a urinary catheter in accordance with the present invention, as defined in the appended claims.

According to a first aspect of the invention there is provided a urinary catheter comprising a tubular shaft extending between a insertable end and a discharge end, and a tip fixedly connected to said insertable end of the tubular shaft, wherein said tip has an outer diameter which at all places is equal to or lower than the outer diameter of the tubular shaft, and wherein the hardness of the tip is equal to or lower than 60 micro Shore A.

The urinary catheter is preferably an intermittent urinary catheter, intended for short time use, such as catheterization of a few minutes duration, being repeated a number of times each day. The term "short term use" indicates a use that is limited in time, and in particular limited to a time period of less than 15 minutes, and preferably less than 10 minutes, and most preferably less than 5 minutes.

The urinary catheter is also preferably a male catheter, preferably having a total length within the range of 35-40 cm, and having an insertable length within the range of 200-350 mm.

It has now surprisingly been found by the present inventors that a tip having an outer diameter which at all places is equal to or lower than the outer diameter of the tubular shaft, such as being conically tapering in a forward direction, and being very soft, so that the hardness of the tip is equal to or lower than 60 micro Shore A, is remarkably easy to insert through an urethra, thereby providing much simplified handling. The soft tip automatically finds it way through the difficult passages of the urethra, and smoothly follows the bends, curves, restrictions and other difficult tracts, and without any risk of penetrating the urethra. The catheter tip adapt to the various anatomical situations as the insertion continues. The force necessary for pushing the catheter through the urethra is hereby also reduced. It has also been surprisingly been found that such a very soft tip, contrary to the previous general belief in the field, has a very limited risk of kinking during insertion. Even in very difficult, and narrow sections, e.g. due to a urethral stricture, no kinking occurs, even when very soft tips are used. For tips having a hardness which is equal to or higher than 20 micro Shore A, the risk of kinking has, surprisingly, been found to be negligible, and it has been found that even extremely soft tips, having an even lower hardness, can be used in most situations. Thus, the present invention not only simplifies the handling of the catheter, but also significantly reduces the risk of injury. Consequently, this catheter is excellently suited for self-catheterization, and can safely and easily be used also by inexperienced users, and/or users suffering from poor dexterity.

Since a catheter with such a soft tip automatically guides it way into the urethra, a lower friction during insertion is also obtained. The risk for penetration of the urethral wall is also lowered, which is of particularly useful for users having no or reduced sensitivity in the urethra tract.

The tip may be straight, extending in the same direction as the tubular shaft and forming a rounded forward end, thereby forming a Nelaton type catheter. However, preferably the tip is curved, forming a Tiemann or Coudé type catheter. Tiemann and Coudé catheters have a tip which is angled upward, to assist in negotiating the male prostatic curve. Thus, this tip form facilitates passage through the bladder neck in the presence of obstruction e.g. from a slightly enlarged prostate gland (e.g. in benign prostatic hyperplasia), and can be helpful for such and other difficult insertions.

The curved tip preferably has a height in a lateral direction which is higher than the diameter of the tube, and preferably the relation K/d, where K is the height of the raised tip and d is the diameter of the tubular shaft, is in the range 1.5-2.

The tip of the catheter forms a free forward end which presents the free forward end of the catheter body, which is spaced apart from the forward end portion of the tubular shaft. Thus, the shaft extends rearwardly from the rear end of the tip portion. A lumen extends through the tubular shaft, from the discharge end to the forward end of the catheter. The lumen ends in drainage openings, so-called eyes, These eyes may be arranged in the forward end of the tubular shaft, in which case the lumen does not need to continue into the tip, which may as a consequence be solid. Alternatively, the eyes may be arranged in the tip, in which case the lumen at least partly continues into the tip.

The tip portion is preferably injection molded, but may also be manufactured in other ways. The tubular shaft may be provided by extrusion, injection molding, etc. For example, the tubular shaft can be an extruded standard tube. This is very beneficial, since extruded tubes are very cost-effective to produce, and also have very good properties, such as a very well-defined and even wall thickness.

The tip has a hardness which is equal to or lower than 50 micro Shore A. Preferably it has a hardness which is equal to or lower than 50 micro Shore A, and more preferably equal to or lower than 45. The tip preferably also has a hardness which is equal to or higher than 20 micro Shore A. Thus, the hardness of the tip is preferably in the range 20-60 micro Shore A, or more preferably in the range 20-50 micro Shore A, and even more preferably in the range 20-45 micro Shore A.

The tip may advantageously have a lower micro Shore A hardness than the tubular shaft, and preferably a micro Shore A hardness that is at least 10% lower, and more preferred at least 30% lower, and most preferably at least 50% lower.

The tip may advantageously be tapering, and preferably continuously tapering, in a direction away from the tubular shaft. The rearward end of the tip preferably has the largest diameter, and this diameter preferably corresponds to the outer diameter of the tubular shaft.

The tip may advantageously have an E-modulus which is lower than the E-modulus of the tubular shaft, and preferably 10-30% lower.

The E-modulus of the tip is preferably within the range 6-16 MPa, and more preferably in the range 9-13 MPa.

The tip may be integrally and monolithically formed with the tubular shaft. In this case the tip may be partly inserted into a lumen opening of the tubular shaft. The tip and tubular shaft may also be produced simultaneously, e.g. by two-component injection molding. Alternatively, the tip may be connected to the tubular shaft by at least one of welding, adhesion and inject molding. In this case, the contacting surfaces of the tip and the tubular shaft are preferably extending at least partly in a longitudinal direction of the catheter, thereby e.g. forming a finger joint or a splice joint.

In order to obtain good properties for handling, painless and easy insertion, etc, the material(s) of the tubular shaft and the tip are preferably prepared and composed in such a way that they fulfills at least some of the following requirements, and preferably essentially all of them:

- The material of the tubular shaft preferably has a hardness adequate for the intended use. Specifically, the micro Shore A hardness should preferably be in the range 75-95, and more preferably in the range 75-90, and most preferably within the range 78-85, for the tubular shaft.
- The material of the tip preferably has a lower hardness than the hardness of the tubular shaft. The micro Shore A hardness of the tip is equal to or lower than 60. Preferably, the micro Shore A hardness of the tip is in the range 10-50, and most preferably within the range 20-45.
- It is further preferred that the materials of both the tip and the tubular shafts have melting temperatures exceeding 90 deg. C., and preferably exceeding 110 deg. C., and most preferably exceeding 130 deg. C.
- It is preferred that the materials are capable of being sterilized by known sterilization methods. In particular it is preferred that the materials have a radiation resistance such that it can endure at least 50 kGy essentially without degradation, in order to enable radiation sterilization of the urinary catheter.
- The material of the tubular shaft should preferably exhibit low resilience.
- The materials, and in particular the material of the tubular shaft, should preferably have good kinking properties.
- The materials are preferably free or essentially free from chlorine or other halogens.
- Preferably, the materials comprise essentially only comprise carbon, hydrogen, nitrogen and oxygen. These constituents should in combination preferably exceed 90% in weight of each material, and preferably exceed 95%. The amount of nitrogen is preferably less than 10%, and most preferably less than 5%.
- The materials should preferably be extrudable, or useable for molding, and in particular useable for injection molding.
- The materials should preferably be biocompatible.

The tip and the tubular shaft may be formed by the same material. The material of the tip and the tubular shaft may have the same or different properties. In case different properties are wanted, this may be accomplished with the use of the same material, e.g. by treatment of the materials in different ways. However, when different properties are wanted in the shaft and the tip, it is preferred to use different or at least partly different materials. For example, the tip can be made softer by using a different blend of polymers, by additives such as plasticizers, medical oil (i.e. oil of a medical grade), paraffin, etc.

The tubular shaft and the tip may be formed of a large variety of different substrate materials. However, preferably the tubular shaft and the tip are made of a polymer material. The tubular shaft and/or the tip may be formed by a polymer blend comprising primarily polyolefin, such as at least 80% by weight of polyolefin and therein possibly intermixed medical oil and/or paraffin. Polyolefin is a material comprising olefin monomers, such as one or several of ethylene, propylene, styrene, pentene, etc. The polyolefin may comprise at least one polymer selected from the group: polyethylene, polypropylene, and styrene block copolymer (SEBS). The polymer blend may further comprise a composition/polymer having molecules with active hydrogen(s), wherein the composition having molecules with active hydrogen(s) is preferably a polymer where the active hydrogen(s) is bound to the polymer via nitrogen.

Molecules with active hydrogen(s) are molecules having hydrogen that is prone to react with other substances, and thus to leave its position in the molecule. Examples of such compositions having molecules with active hydrogen groups are alcohols, amides, amines, urethane and acids. The composition having molecules with active hydrogen(s) is preferably at least one of polyamide and polyurethane. Preferably, the polymer blend comprises a weight percentage of the composition having molecules with active hydrogen(s) in the range of 2-20, and preferably in the range 3-15 and most preferably in the range 5-10. Such polymer blends are known from US 2012/0191073 and U.S. Pat. No. 8,168,249 by the same applicant, said documents hereby being incorporated in their entirety by reference.

However, other materials may also be used, such as polyurethanes, latex rubbers, silicon rubbers, other rubbers, polyvinylchloride (PVC), other vinyl polymers, polyesters, polyacrylates, polyamides, polyolefines, thermoplastic elastomers, styrene block copolymers (SEBS), or polyether block amide (PEBA), and combinations of these.

Still further, the tubular shaft and/or the tip can be made of a degradable material, e.g. of the type disclosed in WO 2011/036162, said document hereby being incorporated in its entirety by reference. The degradable material may e.g. comprise monosaccharide, disaccharide, oligosaccharide and/or polysaccharide. Preferably, the degradable material comprises at least 40% by weight of monosaccharide, disaccharide, oligosaccharide and/or polysaccharide. It is also preferred that the degradable material primarily comprises water and at least one of sugar and starch, and wherein the degradable material preferably comprises at least 90% by weight of said constituents. Additives to control consistency and elasticity may also be incorporated, e.g. a collagen based material such as gelatin. Preferably, the degradable material is such that it becomes essentially totally dissolved if maintained in water at room temperature for at least 6 hours.

For injection molding, a liquid material to be injected is preferably used, such as a thermoplastic material. Suitable thermoplastic materials may be materials such as polyurethane, polyvinyl chloride, polyethylene and other thermoformable materials. The use of thermoplastic materials means that the construction or the shape of the catheter may be partly or fully provided by treating the catheter or the catheter material with heat, such as melting or by solidifying the material by cooling.

The catheter is preferably coated with a hydrophilic surface coating, exhibiting a low friction when wetted. The surface coating is preferably provided at least on an insertable part of the catheter. In case both the tip portion and the shaft, or at least a part of the shaft, is provided with the surface coating, the surface coating may be provided on the tip and the shaft prior to connection of these parts, but is preferably provided after this connection. The coating process may be provided in the way discussed in EP 0 799 069 by the same applicant, said document hereby incorporated in its entirety by reference.

The hydrophilic polymer may be at least one of: polyvinyl compounds, polylactames, in particular such as polyvinyl pyrrolidones, polysaccharides, in particular heparin, dextran, xanthan gum, derivatised polysaccharides, hydroxy propyl cellulose, methyl cellulose, polyurethanes, polyacrylates, polyhydroxyacrylates, polymethacrylates, polyacrylamides, polyalkylene oxides, in particular polyethylene oxides, polyvinyl alcohols, polyamides, polyacrylic acid, copolymers of the previously mentioned polymers, copolymers of vinyl compounds and acrylates or anhydrides, copolymers of vinylpyrrolidone and hydroxy ethylmethyl acrylate, cationic copolymers of polyvinyl pyrrolidone and copolymer of polymethylvinyl ether and maleinic acid anyhydride, polyactide, polyethylene glycol and copolymers thereof. Preferably, the hydrophilic polymer is polyvinyl pyrrolidone.

The hydrophilic coating preferably forms a polyurea network, and most preferably the polyurea network is arranged to form a covalent bond to active hydrogen groups in the substrate. Alternatively, the hydrophilic coating may form an ester bond or an epoxy bond to active hydrogen groups in the substrate.

According to one embodiment, coating of the substrate material of the catheter may be made by a process comprising the steps of: applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature.

However, other hydrophilic coatings are also feasible, such as a coating comprising hydrophilic polymers crosslinked directly to the substrate. The cross-linking may be effected by means of irradiation, e.g. by electron beams or UV light.

The catheter is preferably arranged in a package, to maintain it sterile prior to use.

The catheter preferably has a radiation resistance such that it can endure at least 50 kGy essentially without degradation. Hereby, radiation sterilization of the medical device can be used, without affecting the properties of the medical device.

According to another aspect of the present invention, there is provided a method for producing a urinary catheter, comprising:

providing a tubular shaft extending between a insertable end and a discharge end of the catheter;

providing a tip having an outer diameter which at all places is equal to or lower than the outer diameter of the tubular shaft, and wherein the hardness of the tip is equal to or lower than 60 micro Shore A; and fixedly connecting the tip to the insertable end of the tubular shaft.

Hereby, similar advantages and properties are obtained as discussed above in relation to the first and second aspects of the invention.

These and other aspects of the inventive concept will be apparent from and elicited with reference to the embodiments described hereinafter.

BRIEF DESCRIPTION OF THE DRAWINGS

By way of example embodiments of the invention will now be described with reference to the accompanying drawings in which.

DESCRIPTION OF PREFERRED EMBODIMENTS

Figure 1:
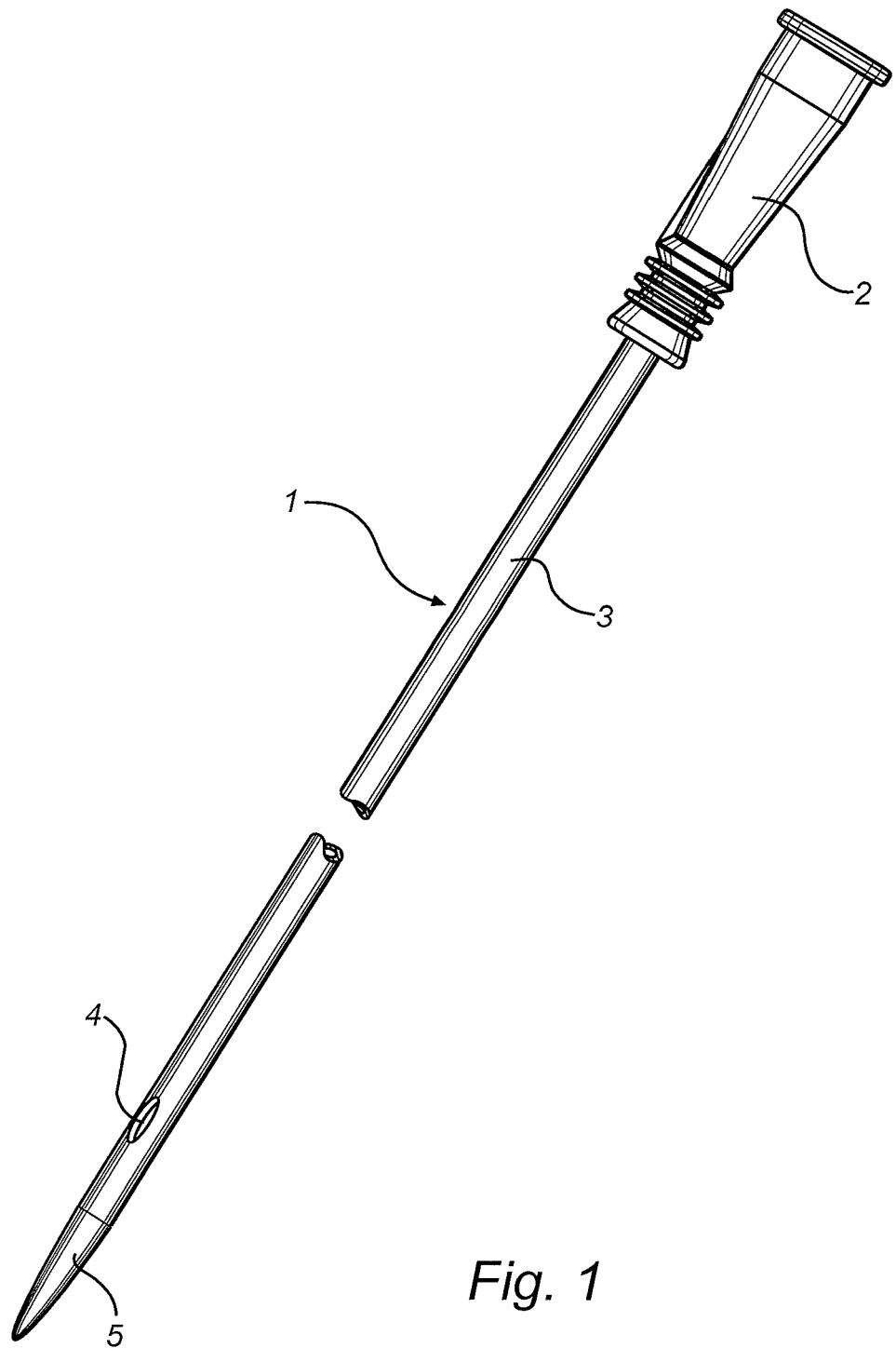
FIG. 1 illustrates an embodiment of a catheter according to the invention.

In the following detailed description preferred embodiments of the invention will be described. However, it is to be understood that features of the different embodiments are exchangeable between the embodiments and may be combined in different ways, unless anything else is specifically indicated. It may also be noted that, for the sake of clarity, the dimensions of certain components illustrated in the drawings may differ from the corresponding dimensions in real-life implementations. Even though in the following description, numerous specific details are set forth to provide a more thorough understanding of the present invention, it will be apparent to one skilled in the art that the present invention may be practiced without these specific details. In other instances, well known constructions or functions are not described in detail, so as not to obscure the present invention.

The following discussion is in particular concerned with hydrophilic urinary catheters for intermittent use. However, the invention can also be used in relation to other types of urinary catheters.

A catheter 1 as illustrated in FIG. 1, comprises a flared rearward portion 2 and an elongate shaft or tube 3 projecting forwardly from the rearward portion 2. An open-ended internal lumen extends from the rear end of the rearward portion 2 to one or more drainage apertures 4 in a forward end of the catheter. At the forward end of the elongate shaft 3, a tapering tip 5 is arranged, having a rounded tip end. The rearward portion 2 may function as a connector of the catheter 1, being connectable to other devices, such as a urine collection bag, a drainage tube or the like.

The drainage openings may be arranged in the forward end of the tubular shaft, in which case the lumen does not need to continue into the tip, which may as a consequence be solid. Alternatively, the eyes may be arranged in the tip, in which case the lumen at least partly continues into the tip.

At least a part of the elongate tube 3 forms an insertable length to be inserted through a body opening of the user, such as the urethra in case of a urinary catheter. By insertable length is normally meant that length of the elongate tube 2 which is insertable into the urethra of the patient during ordinary use. In case a hydrophilic catheter is used, the insertable length is coated with a hydrophilic material, for example PVP, or is made of hydrophilic material. Typically, the insertable length is 80-140 mm for a female patient and 200-350 mm for a male patient.

Figure 2:
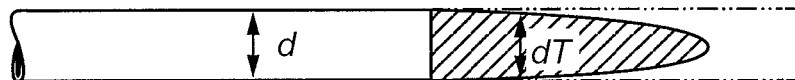
FIG. 2 is a more detailed cross-sectional view of the catheter tip in the catheter of FIG. 1.

The tip may be straight, extending in the same direction as the tubular shaft and forming a rounded forward end, thereby forming a Nelaton type catheter. Such an embodiment is illustrated in FIGS. 1 and 2. The tip has an outer diameter dT which at all places is equal to or lower than the outer diameter d of the tubular shaft. The tip is preferably arranged conically tapering in the forward direction, to end in a rounded tip. However, alternative configurations are also feasible. For example, the tip may over part of its extension have a cylindrical configuration with the same diameter, may be arranged in a stepwise reduced diameter, may have parts being slightly enlarged, such as a ball shaped forward end, or the like. For example, the end may be provided with a slightly enlarged rounded or ball-shaped head portion, which, however, has at least a slightly smaller diameter than the diameter of the tube.

Figure 3:
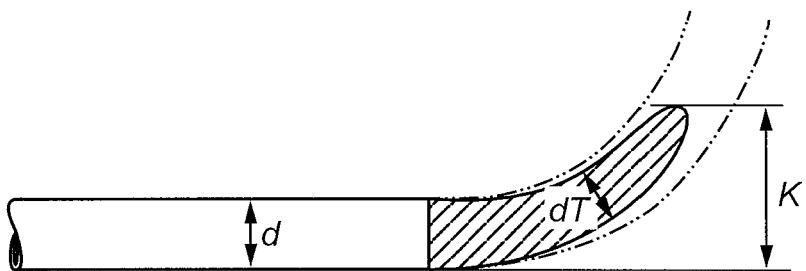
FIG. 3 is a cross-sectional view of a curved tip configuration, in accordance with another embodiment of the present invention.

The tip may also be curved, forming a Tiemann or Coudé type catheter. Such a tip is illustrated in FIG. 3. The curved tip also has a diameter dT which at all places is equal to or lower than the outer diameter d of the tubular shaft. The curved tip preferably has a height K in a lateral direction which is higher than the diameter d of the tube, and preferably the relation K/d is in the range 1.5-2.

The tips may be designed and connected to the tubular shaft in various ways, and some exemplary embodiments of this will now be discussed with reference to FIGS. 4a-e. The tip preferably connects with the same outer diameter to the tube, thereby providing an outer transition area without steps, edges or the like.

Figure 4A:
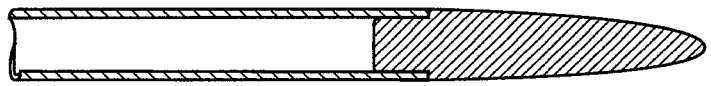
FIGS. 4a-f are cross-sectional views of various tips in accordance with embodiments of the present invention.

The tip of the catheter forms a free forward end which presents the free forward end of the catheter body, which is spaced apart from the forward end portion of the tubular shaft. Thus, the shaft extends rearwardly from the rear end of the tip portion. A lumen extends through the tubular shaft, from the discharge end to the forward end of the catheter. The lumen ends in drainage openings, so-called eyes, These eyes may be arranged in the forward end of the tubular shaft, in which case the lumen does not need to continue into the tip, which may as a consequence be solid. Examples of such tip configurations are illustrated in FIGS. 4a, 4b, 4d and 4f. Alternatively, the eyes may be arranged in the tip, in which case the lumen at least partly continues into the tip, as in FIG. 4c. It is also possible to use a lumen partly extending into the tip, even though the drainage eyes are provided in the tubular shaft, as illustrated in the embodiment of FIG. 4e. Hereby, the tip can be made more flexible, and less material is needed for producing the tip.

The tip may be integrally and monolithically formed with the tubular shaft. In this case the tip may be partly inserted into a lumen opening of the tubular shaft. Such an embodiment is illustrated in FIG. 4a. The tip and tubular shaft may also be produced simultaneously, e.g. by two-component injection molding.

The connector, i.e. the flared rearward portion 2 is optional, and catheters without any flared rearward portion may also be used. In case a flared connector is used, this may be formed integrally and monolithically at the rearward end of the tubular shaft. However, it may also be formed as a separate component, being connected to the tubular shaft by means of welding, adhesion or the like. It may also be inject molded directly in place. In this case, the inject molding of the tip at the forward end of the tubular shaft and the connector at the rearward end of the tubular shaft can be performed simultaneously.

In order to provide a stronger connection between the tip and the tubular shaft, the outer surface of the inserted tip, and/or the corresponding inner surface of the tubular shaft, may be provided with a surface texture or surface features, and preferably a texture/feature matching each other to form a mechanical engagement. For example, the tip may be provided with outwardly protruding elements, such as a dent, bump, ridge or the like, and the tubular shaft may be provided with corresponding indent elements, such as holes, grooves or the like. However, naturally the protruding elements can be arranged on the tubular shaft instead, or a combination of protruding and indent elements be provided on both parts. Such an embodiment is schematically illustrated in FIG. 4f.

Alternatively, the tip may be connected to the tubular shaft by at least one of welding, adhesion and inject molding. In the embodiment of FIG. 4d, the connection is made on surfaces extending entirely perpendicular to the longitudinal direction of the catheter.

Figure 4B:
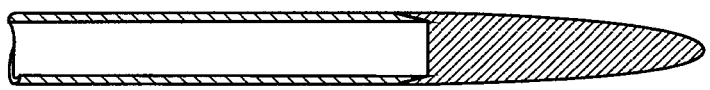
Figure 4C:
Figure 4D:
Figure 4E:
Figure 4F:
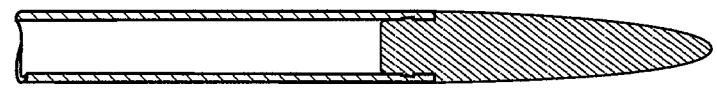

However, in order to increase the strength of the joint, the contacting surfaces of the tip and the tubular shaft may also extend at least partly in a longitudinal direction of the catheter, thereby e.g. forming a finger joint, as illustrated schematically in FIG. 4c, or a splice joint, as illustrated schematically in FIGS. 4b and 4e.

The catheter can be un-coated, and can e.g. be used together with a gel lubricant or the like for insertion. The catheter may also be formed by a material having low friction, and can e.g. be made by a hydrophilic material. However, the catheter is preferably coated, as have been discussed in the foregoing. In particular, for catheters, it is preferred to coat the outer surface, at least of the insertable part, with a hydrophilic coating. Many different types of well-known hydrophilic surfaces can be used.

Some preferred examples of methods for applying a hydrophilic surface coating to the tubular shaft and/or the tip will now be discussed in greater detail. However, it is to be noted that the many other methods for obtaining a hydrophilic surface coating can also be used.

In one embodiment, the entire or part of the outer surface of the catheter is coated with a stable hydrophilic coating by applying sequentially to the surface of the substrate first a solution comprising between 0.05 to 40% (weight to volume) of an isocyanate compound and thereafter a solution containing between 0.5 and 50% (weight to volume) of polyvinylpyrrolidone and curing at an elevated temperature. The isocyanate solution may advantageously contain between 0.5 to 10% (weight to volume) of the isocyanate compound, and may preferably contain between 1 to 6% (weight to volume) of the isocyanate compound. Generally, the isocyanate solution only needs to be in contact with the surface briefly, for example 5 to 60 sec.

Application of the isocyanate solution to the catheter surface results in a coating having unreacted isocyanate groups being formed on the substrate surface. Application of the polyvinylpyrrolidone solution to the catheter surface then results in a hydrophilic polyvinylpyrrolidone-polyurea interpolymer coating being formed. Curing of this hydrophilic coating binds the isocyanate compounds together to form a stable non-reactive network that binds the hydrophilic polyvinylpyrrolidone. To advantage, curing takes place in the presence of a water-containing gas, for example ambient air, to enable the isocyanate groups to react with the water to yield an amine which rapidly reacts with other isocyanate groups to form a urea cross-link. Further, the method may comprise the steps of evaporating the solvent of the isocyanate solution prior to application of the polyvinylpyrrolidone solution and evaporating the solvent of the polyvinylpyrrolidone solution prior to curing of the hydrophilic coating. This may for example be done by air drying.

The isocyanate compound preferably comprises at least two unreacted isocyanate groups per molecule. The isocyanate may be selected from 2,4-toluene diisocyanate and 4,4'-diphenylmethane diisocyanate, or a pentamer of hexamethylene diisocyanate and toluene diisocyanate of cyanurate type, or trimerized hexamethylene diisocyanate biuret or mixtures thereof.

The solvent for the isocyanate compound is preferably one which does not react with isocyanate groups. A suitable solvent is methylene chloride but it is also possible to use ethyl acetate, acetone, chloroform, methyl ethyl ketone and ethylene dichloride, for example.

In order to shorten the necessary reaction times and curing times suitable catalysts for isocyanate curing may be added. These catalysts may be dissolved in either the isocyanate solution or the polyvinylpyrrolidone solution but are preferably dissolved in the latter. Different types of amines are especially useful, for example diamines, but also for example triethylenediamine. Preferably, an aliphatic amine is employed which is volatisable at the drying and curing temperatures used for the coating, and which furthermore is non-toxic. Examples of suitable amines are N,N'diethylethylendiamine, hexamethylendiamine, ethylendiamine, paradiaminobenzene, 1,3-propandiol-para-aminobenzoic acid diester and diaminobicyclo-octane.

The polyvinylpyrrolidone used preferably has a mean molecular weight of between 104 to 107 with the most preferred mean molecular weight being about 105. Polyvinylpyrrolidone having such a molecular weight is commercially available, for example under the trademark Kollidon® (BASF). Examples of suitable solvents for polyvinylpyrrolidone that may be used are methylene chloride, ethyl acetate, acetone, chloroform, methyl ethyl ketone and ethylene dichloride. The proportion of polyvinylpyrrolidone in the solution is preferably between 0.5 to 10% (weight to volume) and most preferred between 2 to 8% (weight to volume). The polyvinylpyrrolidone in the solvent is applied by dipping, spraying or the like for a short period of time, e.g. during 5 to 50 sec.

Curing of the coating is preferably performed at a temperature of 50 to 130 deg. C., in for example an oven, for a duration of between 5 to 300 min.

In a preferred embodiment the hydrophilic coating contains an osmolality-increasing compound, for instance an inorganic salt selected from sodium and potassium chlorides, iodides, citrates and benzoates. The osmolality-increasing compound may be applied in the manner detailed in EP 0 217 771 by the same applicant.

In case a hydrophilic coating is used, it is preferred that both the tip and an insertable part of the tubular shaft are provided with said coating. The coating may be applied after joining of the tip and the tubular shaft, but may alternatively be provided separately to the tip and the tubular shaft, prior to joining.

Upon use, the catheter, when being provided with a hydrophilic coating, or being made by a hydrophilic material, is wetted by a wetting fluid, whereby the hydrophilic surface becomes slippery and easy to insert into e.g. the urethra of the patient, i.e. to provide a low-friction character of the surface. The wetting fluid is preferably a water-based liquid, i.e. using water as a solvent.

Experiments

In the catheters used for the experimental tests relating to embodiments of the present invention, the tubular shafts were made by a material commercially available under the trade name Meliflex M6504 by Melitek, and which is a polyolefin thermoplastic elastomer, with a composition generally in accordance with the previously discussed polyolefin based materials. This material is in the following referred to as material A. The catheter tubes were of 40 cm length, and had a size of Ch 12.

The tips for these catheters were made of four different materials. The tips all had the same conically tapering geometry, in accordance with the discussion above.

The tips were made by the following materials, respectively:

Material B, which is a commercially available thermoplastic elastomeric material sold under the trade name Dryflex 500400S by Elasto. This material is primarily based on SEBS.

Material C, which is a commercially available thermoplastic elastomeric material sold under the trade name Meliflex M7940 by Melitek, and which is a soft TPE with good moulding properties.

Material D, which is a commercially available thermoplastic elastomeric material sold under the trade name Dryflex 500122 by Elasto. This material is primarily based on TPS-SEBS.

As a comparative example, a commercially available catheter from Manfred Sauer, sold under the trade name IQ-Cath, was used. This is a PVC-based catheter, having an enlarged, ball-shaped tip, in accordance with the disclosure in the above-discussed patent application US 2004/193143. These catheters were also of the size Ch 12.

In one line of experimental tests, the E-modulus of the tubular shafts and tips were determined. To this end, measurements were made generally in accordance with the standard ASTM D 638. However, since this standard requires relatively long samples, the test was slightly modified to make it possible to measure on short samples, such as the tips of the catheters. The tips here had a length in the range 30-50 mm. The sample was clamped between two clamping jaws. The clamping jaws were initially separated by 2 mm. After initial clamping, the samples were maintained in this position for a minute, for conditioning and relaxation of the material.

Thereafter, the measurement parameters were reset, and measurements were made by pulling the clamping jaws apart. The pulling speed was set to 10 mm/min, and pulling was continued until the jaws were stretched apart by 5 mm. The pulling force was measured after 0.05 mm and 0.25 mm. The E-modulus was then calculated in accordance with the following formula:

$$E=[4*L_0*(X_H-X_L)]/[\pi*(d_a^2-d_i^2)*(L_H-L_L)]$$

where E is the tensile modulus (also known as Young's modulus) in kN/mm², $L_0$ is the initial gage length in mm, $X_H$ is the end of tensile in kN, $X_L$ is the being of tensile in kN, $\pi$ is a constant (3.14159), $d_a$ is the outer diameter in mm, $d_i$ is the inner diameter in mm, $L_H$ is the strain in mm at $X_H$, and $L_L$ is the strain in mm at $X_L$.

Further, the hardness was measured. Due to the limited size of the samples, the hardness was measured in micro Shore A (μShA). The measurements were made with a commercially available measurement device, the Bareiss Shore meter Digitest II, provided with a micro Shore A tip. The measurements were made in accordance with the standard ASTM D 2240. Measurements were made at different positions along the samples. The tips were solid, and could be measured directly. The tubular shafts were provided with a steel rod in the lumen, and a cut open second tube was arranged on top of the first tube, in order to obtain sufficient thickness.

Still further, insertion of the catheters into an artificial urethra, having an artificial sphincter was tested. The artificial urethra comprised a large container, simulating the bladder, a tube connected to an inlet of the container, simulating the urethra, and a porous member with a through bore having 4 mm in diameter arranged in the inlet of the bladder, simulating the sphincter. The porous member was made by using conventional foam ear plugs.

The results of the E-modulus measurements are presented in the following table 1:

TABLE 1

E modulus [MPa] for different materials, and for tip and shaft

|  | Mat. B tip | Mat. C tip | Mat. D tip | IQ-Cath tip | Mat. A shaft | IQ-Cath shaft |
|---|---|---|---|---|---|---|
| Mean | 11.178 | 10.750 | 6.782 | 17.604 | 13.089 | 26.895 |
| Std dev. | 1.4880 | 0.7486 | 1.1711 | 1.4037 | 0.7734 | 0.8703 |
| Max | 13.360 | 12.062 | 8.670 | 19.713 | 14.021 | 28.099 |
| Min | 9.395 | 10.207 | 5.581 | 15.932 | 12.339 | 26.025 |

The results of the micro Shore A measurements are presented in the following table 2:

TABLE 2

Hardness [μShA] for different materials, and for tip and shaft

|  | Mat. B tip | Mat. C tip | Mat. D tip | IQ-Cath tip | Mat. A shaft | IQ-Cath shaft |
|---|---|---|---|---|---|---|
| Mean | 40.23 | 40.23 | 13.58 | 52.63 | 81.65 | 91.79 |
| Std dev. | 0.818 | 0.612 | 0.121 | 2.547 | 0.858 | 1.832 |
| Max | 41.10 | 41.00 | 13.67 | 55.13 | 82.77 | 93.57 |
| Min | 39.27 | 39.47 | 13.43 | 49.60 | 80.43 | 89.17 |

In the insertion test in the artificial urethra, it was found that the IQ-cath could not be introduced through the narrow opening simulating the sphincter, and failed in all the tests. However, the catheters made in accordance with the invention could find their way into this narrow passage. From this is was generally concluded that the usability and maneuver properties of the new catheters are very good. More specifically, the catheters having tips of material B and C could pass the defined obstacle at all tested occasions. The catheters having the very soft tip of material D passed the narrow passage at many occasions, but sometimes had a tendency of bending at the top, thereby stopping the insertion. This catheter with the tip of material D passed the test at about 40% of the tests.

Based on the above discussed experimental results, the following conclusions can be drawn:

The catheter tips of materials B-D all have a micro Shore A hardness much lower than that of the shaft.

The shafts made of material A and PVC (IQ-Cath) had a micro Shore A hardness exceeding 80.

The catheter tips made of materials B-D had a micro Shore A hardness in the range 13.58-40.23.

Based on this, the conclusion is reached that tips made of materials having a micro Shore A hardness equal to or below 60, and preferably equal to or lower than 50, and more preferably equal to or lower than 45 are very useful and show advantageous properties.

Since the very soft tip made of material D had problems of passing the very difficult obstacle in the artificial urethra test, is also assumed that the tip material should preferably have a micro Shore A hardness exceeding 20.

The E-modulus of the tips made of materials B-D are in the range 6.8-11.2 MPa.

The E-modulus of the tip in the IQ-cath (17.6 MPa), and in the shafts made of material A (13.1 MPa) and PVC in the IQ-Cath (26.9 MPa) are all much higher than in the tips made of materials B-D.

Based on this, the conclusion is reached that tips made of materials having an E-modulus equal to or lower than 16 MPa, and preferably equal to or lower than 13 MPa are very useful and show advantageous properties.

Since the very soft tip made of material D had problems of passing the very difficult obstacle in the artificial urethra test, is also assumed that the tip material should preferably have an E-modulus equal to or higher than 9 MPa.

Based on this, the conclusion is reached that tips made of materials having an E-modulus in the range 6-16 MPa, and preferably in the range 9-13 MPa are very useful and show advantageous properties.

The person skilled in the art realizes that the present invention by no means is limited to the preferred embodiments described above. On the contrary, many modifications and variations are possible within the scope of the appended claims. For instance, the tip need not be continuously tapering, but have other geometrical shapes. Further, the tip may be either straight, pointing directly in the longitudinal direction of the catheter, or be slightly curved, so that the end of the tip points in a direction which is non-parallel to the longitudinal direction of the catheter. Further, many different materials and material combinations may be used to produce the tubular shaft and the tip, and still obtain the desired material properties. Still further, the access openings/drainage eyes may be provided in either the tip or in the forward end of the tubular shaft, or even in both. Such and other modifications should be construed to fall within the scope of the appended claims.

We claim:

1. A urinary catheter comprising a tubular shaft extending between an insertable end and a discharge end, and a tip fixedly connected to said insertable end of the tubular shaft, wherein said tip is solid and has an outer diameter which at all places is equal to or smaller than the outer diameter of the tubular shaft, and comprises a part tapering in a direction away from the tubular shaft, and a rounded end part, and wherein a hardness of the tip is within the range 20-60 micro Shore A, an E-modulus of the tip is within the range 6-16 MPa, and the tip has a micro Shore A hardness which is lower than the micro Shore A hardness of the tubular shaft, wherein the tubular shaft has a micro Shore A hardness within the range 75-95 micro Shore A, and wherein the urinary catheter is a hydrophilic urinary catheter with a single lumen.

2. The urinary catheter of claim 1, wherein the tip is curved and angled upwards.

3. The urinary catheter of claim 1, wherein the hardness of the tip is equal to or lower than 50 micro Shore A.

4. The urinary catheter of claim 1, wherein the hardness of the tip is equal to or lower than 45 micro Shore A.

5. The urinary catheter of claim 1, wherein the hydrophilic urinary catheter is at least partly provided with a hydrophilic surface coating, said hydrophilic surface coating exhibiting a reduced friction when wetted.

6. The urinary catheter of claim 1, wherein the hydrophilic urinary catheter is made of a hydrophilic material.

7. The urinary catheter of claim 1, wherein the tip has a micro Shore A hardness that has at least 10% lower than a micro Shore A hardness of the tubular shaft.

8. The urinary catheter of claim 1, wherein the tip has a micro Shore A hardness that is at least 30% lower than a micro Shore A hardness of the tubular shaft.

9. The urinary catheter of claim 1, wherein the tip has a micro Shore A hardness that is at least 50% lower than a micro Shore A hardness of the tubular shaft.

10. The urinary catheter of claim 1, wherein the tip is continuously tapering in a direction away from the tubular shaft.

11. The urinary catheter of claim 1, wherein the tip has an E-modulus which is lower than the E-modulus of the tubular shaft.

12. The urinary catheter of claim 1, wherein the tip has an E-modulus which is 10-30% lower than the E-modulus of the tubular shaft.

13. The urinary catheter of claim 1, wherein the E-modulus of the tip is within the range 9-13 MPa.

14. The urinary catheter of claim 1, wherein the tip is integrally and monolithically formed with the tubular shaft.

15. The urinary catheter of claim 1, wherein the tip is partly inserted into a lumen opening of the tubular shaft.

16. The urinary catheter of claim 1, wherein the tip is connected to the tubular shaft by at least one of welding, adhesion or injection molding.

17. The urinary catheter of claim 15, wherein the contacting surfaces of the tip and the tubular shaft are extending at least partly in a longitudinal direction of the catheter.

18. The urinary catheter of claim 17, wherein the contacting surfaces of the tip and the tubular shaft form at least one of a finger joint or a splice joint.

19. The urinary catheter of claim 1, wherein the tip and the tubular shaft are formed of different materials.

20. The urinary catheter of claim 2, wherein the tip has a height in a lateral direction which is higher than the diameter of the tubular shaft.

21. The urinary catheter of claim 20, wherein a relation K/d is in the range 1.5 to 2, where K is the height of the tip and d is the diameter of the tubular shaft.

22. The urinary catheter of claim 1, wherein the end part forms a ball-shaped head portion.

23. A urinary catheter comprising a tubular shaft extending between an insertable end and a discharge end, and a tip fixedly connected to said insertable end of the tubular shaft, wherein said tip is solid and has an outer diameter which at all places is equal to or smaller than the outer diameter of the tubular shaft, and comprises a part tapering in a direction away from the tubular shaft, and wherein a hardness of the tip is within the range 10-50 micro Shore A, an E-modulus of the tip is within the range 6-16 MPa, and a hardness of the tubular shaft is within the range 75-95 micro Shore A, and wherein the urinary catheter is a hydrophilic urinary catheter with a single lumen.

24. A urinary catheter comprising a tubular shaft extending between an insertable end and a discharge end, and a tip fixedly connected to said insertable end of the tubular shaft, wherein said tip is solid and has an outer diameter which at all places is equal to or smaller than the outer diameter of the tubular shaft, and comprises a part tapering in a direction away from the tubular shaft, and wherein a hardness of the tip is within the range 20-60 micro Shore A, an E-modulus of the tip is within the range 6-16 MPa, and the tip has a micro Shore A hardness which is lower than the micro Shore A hardness of the tubular shaft.

* * * * *